United States Patent [19]

Ersek

[11] 4,378,802
[45] Apr. 5, 1983

[54] SEPTAL SPLINT

[76] Inventor: Robert A. Ersek, 2300 Cypress Point West, Austin, Tex. 78746

[21] Appl. No.: 265,963

[22] Filed: May 21, 1981

[51] Int. Cl.³ .............................................. A61B 17/00
[52] U.S. Cl. ................................................... 128/346
[58] Field of Search .................. 128/76 R, 76 C, 342, 128/343, 89 R, 83, 346, 325, 87 R, 89 A

[56] References Cited

U.S. PATENT DOCUMENTS

| | | | |
|---|---|---|---|
| 2,015,617 | 9/1935 | Claudius | 128/346 |
| 2,202,748 | 5/1940 | Solo | 128/342 X |
| 2,509,157 | 5/1950 | Lind | 128/89 A |
| 2,757,665 | 8/1956 | Tanikawa | 128/346 X |
| 3,349,771 | 10/1967 | Baer | 128/325 |
| 4,105,035 | 8/1978 | Rella | 128/342 |

Primary Examiner—John D. Yasko
Attorney, Agent, or Firm—Orrin M. Haugen; Thomas J. Nikolai

[57] ABSTRACT

A septal splint comprising a clip member to which a pair of plate members are secured to extend in spaced relation in the same direction, and apply pressure to both sides of the nasal septum, when trimmed to a desired shape and inserted in a patient's nostrils. The clip member has a central loop which remains external of the patient and may be severed to facilitate removal of the splint after use.

2 Claims, 7 Drawing Figures

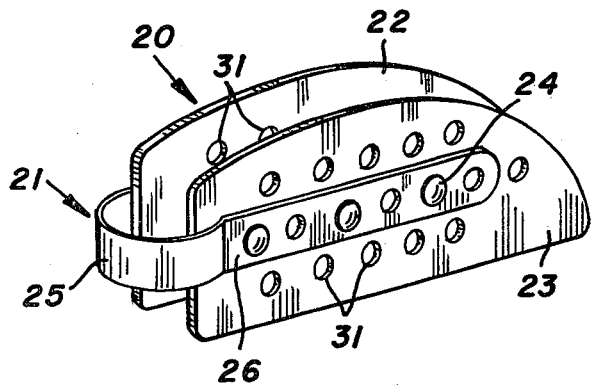
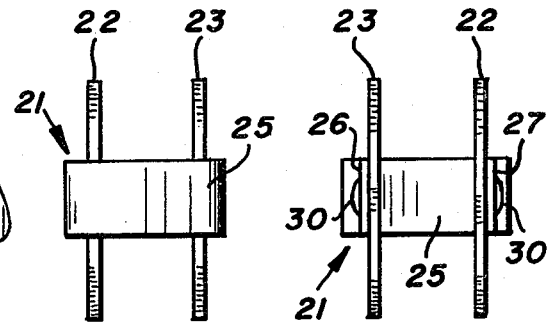
FIG.1  FIG.2  FIG.3
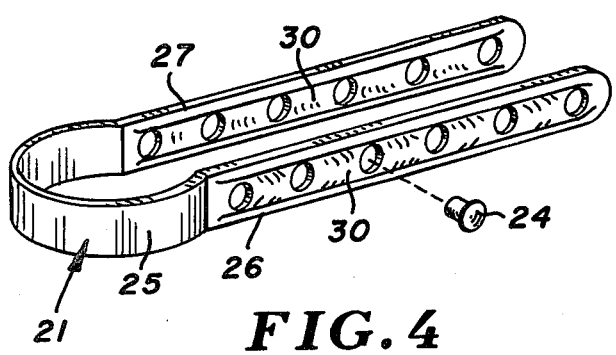
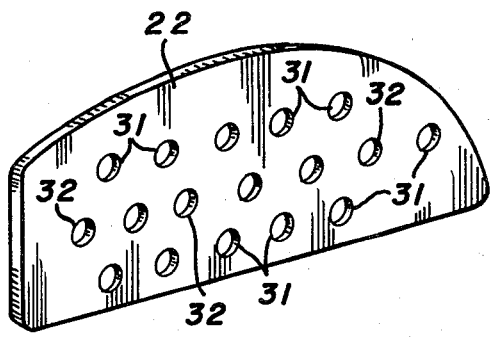
FIG.4  FIG.5
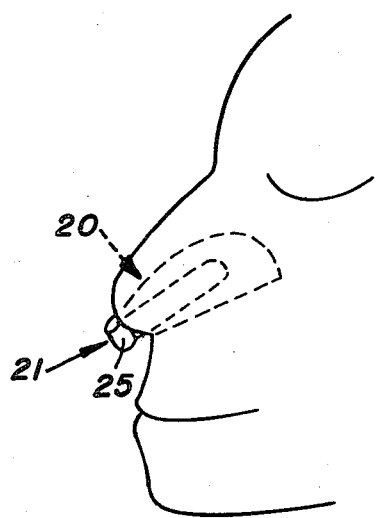
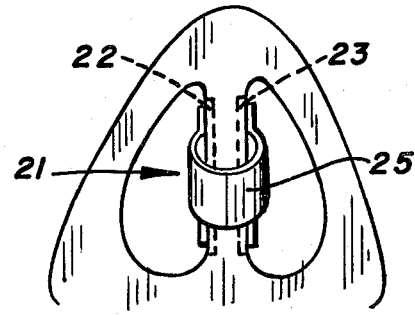
FIG.6  FIG.7

SEPTAL SPLINT

FIELD OF THE INVENTION

This invention relates to the field of surgery, and more particularly to surgery directed to the repair of injuries or defects in the human nasal septum.

BACKGROUND OF THE INVENTION

In the practice of nasal reconstructive surgery, it is often necessary to provide support to the septum of the nose. This may be done merely by packing the nose with gauze or inflatable balloons, but these expedients do not insure that the septum itself will be supported, or will remain straight or symmetrical. Another technique includes cutting pieces of a material such as polyethylene sheet to the shape of the septum on both sides, placing the pieces within the nostrils, and passing transfixion stitches through the septum and the two pieces of material in order to provide an external framework for the septum. This procedure sometimes results in necrosis of the septum or its mucosal lining, or accumulation of blood or mucus under the plastic pieces. It also frequently occurs that removal of the stitches and the plastic pieces causes disruption of recently-repaired tissues, and can be made difficult by crusting or adhesion.

SUMMARY OF THE INVENTION

The present invention comprises a splint which can be inserted into the nose to apply moderate pressure to both sides of the septum without exceeding capillary pressure, which is aesthetically acceptable to the patient, and which is readily removable when its use is no longer needed.

Various advantages and features of novelty which characterize the invention are pointed out with particularity in the claims annexed hereto and forming a part hereof. However, for a better understanding of the invention, its advantages, and objects obtained by its use, reference should be had to the drawing which forms a further part hereof, and to the accompanying descriptive matter, in which there is illustrated and described a preferred embodiment of the invention.

BRIEF DESCRIPTION OF THE DRAWING

In the drawing, in which like reference numerals indicate corresponding parts throughout the several views, FIG. 1 is a perspective view of a splint according to the invention;

FIGS. 2 and 3 are end views of the splint of FIG. 1 seen from the left and right respectively;

FIGS. 4 and 5 are views in perspective of a clip member and a plate member which are portions of the invention;

FIG. 6 is a lateral view of a splint in place, shown schematically; and

FIG. 7 is a nostril view showing a splint in place.

DESCRIPTION OF THE PREFERRED EMBODIMENT

A septal splint 20 according to the invention is shown in FIG. 1 to comprise a clip member 21 and a pair of plate members 22 and 23 connected to the clip member by fasteners such as rivets 24. Clip member 21 is formed of a strip of material such as aluminum having a central loop 25 from which a pair of parallel struts 26 and 27 extend in the same direction, the struts being spaced by less than the diameter of the loop which extends peripherally through more than 180°. If desired, the material of loop 25 may be wider than that of struts 26 and 27, which latter may also be reinforced by ribs 30. The struts include a plurality of drainage holes having a predetermined spacing therebetween.

Plate members 22 are preferably of plastic thick enough to be reasonably rigid yet easily shaped with scissors to the desired septal outline. They are provided with fields of apertures 31 for passage of sutures or for drainage, and with further apertures 32 to receive rivets 24 by which the plate members are secured to the inner surfaces of struts 26 and 27. Polyethylene is suitable for use in plates 22, as it is smooth, easily shaped, and benign and non-adhesive to human tissue. The spacing between holes 31 corresponds to the spacing between holes in struts 26 and 27 to provide unobstructed drainage paths, all as illustrated in FIG. 1.

In use, the splint is sterilized and placed in the nose after reconstructive surgery has been completed, by spreading the clip member, passing the plates into the nose on opposite sides of the septum, and allowing the clip to return to its preformed shape. Loop 25 is large enough to encircle the patient's columella, and the spacing between plates 22 is such, three millimeters, for example, as to apply moderate pressure, to both sides of the septum, sufficient to give adequate support and yet not in excess of capillary blood pressure (25 mm of mercury). Drainage apertures 31 prevent the accumulation of blood or mucus under the plates, and also enable the insertion of transfixion stitches if this procedure is elected. The patient's nostrils may thereafter be packed with gauze if desired.

It will be evident that after application, the splint is only minimally noticeable, a significant aesthetic consideration. When it is desired to remove the splint, loop 25, which remains external, is grasped with a surgical instrument or the fingers of the surgeon, and the loop is cut with surgical scissors, releasing the pressure on the septum and facilitating the removal of the two plate members independently, thus minimizing any trauma of removal.

From the above, it will be evident that the invention comprises a septal splint which is easily shaped to fit a particular need, conveniently applied, self-retaining or suturable as desired and which supports the septum with a minimum likelihood of necrosis, encrustment or adhesion, and with maximum ease of removal without trauma.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

I claim:

1. A septal splint for post-operative bilateral support of a human nasal septum comprising a resilient clip member, a pair of plate members sized for insertion in a patient's nostrils, and fastening means securing the plate members to the clip member, said clip member comprising a strip of resilient material formed as a central loop and having a pair of flat parallel struts extending in the same direction from the loop for a distance related to the length of the human nasal septum, and having spaced apposed inner surfaces, said struts being provided with drainage holes, said plate members being of thin rigid material which is benign and non-adherent to human mucosa, and being formed with fields of drainage holes communicating with said drainage holes in said struts, said fastening means securing said plate members to the inner faces of said struts, and the spacing between said plate members and the resilience of said clip member being such that when said plate members are inserted into the nostrils of a patient, said plate members engage the sides of the nasal septum with a continuous pressure less than capillary blood pressure.

2. A splint according to claim 1 in which the diameter of said loop is greater than the space between said plate members, and is greater than the width of the human columnella.

* * * * *